(12) United States Patent
Bloesl et al.

(10) Patent No.: US 8,861,676 B2
(45) Date of Patent: Oct. 14, 2014

(54) TRANSPORT BIN IN AN X-RAY INSPECTION SYSTEM

(75) Inventors: Harald Bloesl, Kelkheim (DE); Uwe Flehmig, Wiesbaden (DE); Christian Haas, Kelkheim (DE); Claus Meder, Rossdorf (DE); Dirk Naumann, Lorsch (DE); Daniel Schmitt, Loef (DE)

(73) Assignee: Smiths Heimann GmbH, Wiesbaden (DE)

( * ) Notice: Subject to any disclaimer, the term of this patent is extended or adjusted under 35 U.S.C. 154(b) by 0 days.

(21) Appl. No.: 13/440,665

(22) Filed: Apr. 5, 2012

(65) Prior Publication Data

US 2012/0189097 A1 Jul. 26, 2012

Related U.S. Application Data

(63) Continuation of application No. PCT/EP2010/005580, filed on Sep. 11, 2010.

(30) Foreign Application Priority Data

Oct. 8, 2009 (DE) .......................... 10 2009 048 770

(51) Int. Cl.
*G01N 23/04* (2006.01)
*G01V 5/00* (2006.01)
*G21K 5/08* (2006.01)
*G01T 7/08* (2006.01)
*B65D 1/34* (2006.01)

(52) U.S. Cl.
CPC ........ *G01V 5/0016* (2013.01); *G01N 2223/307* (2013.01); *G21K 5/08* (2013.01); *G01T 7/08* (2013.01); *B65D 1/34* (2013.01); *B65D 2203/10* (2013.01)

USPC ............................... 378/57; 378/165; 378/208

(58) Field of Classification Search
CPC .............. G01N 23/04; G01N 2223/30; G01N 2223/307; G01V 5/00; G01V 5/0008; G01V 5/0016; G01T 7/00; G01T 7/02; G01T 7/08; G01T 7/12; G21K 5/08
USPC ..................... 378/57, 114, 162, 165, 208, 210
See application file for complete search history.

(56) References Cited

U.S. PATENT DOCUMENTS

| 2002/0176531 | A1 | 11/2002 | McClelland et al. |
| 2005/0111618 | A1 | 5/2005 | Sommer, Jr. et al. |
| 2007/0132580 | A1 | 6/2007 | Ambrefe |
| 2012/0114103 | A1* | 5/2012 | Aust et al. ..................... 378/98.2 |
| 2012/0189097 | A1* | 7/2012 | Bloesl et al. ..................... 378/57 |

FOREIGN PATENT DOCUMENTS

DE    10 2009 015 606 A1    10/2010

OTHER PUBLICATIONS

"Universally unique identifier", Sep. 29, 2009, retrieved from the Internert, XP000002659260.

* cited by examiner

*Primary Examiner* — Thomas R Artman
(74) *Attorney, Agent, or Firm* — Muncy, Geissler, Olds & Lowe, P.C.

(57) ABSTRACT

A transport bin for an X-ray inspection system, comprising a identifying device rigidly connected to the bin, the identifying device having a bin-specific identifier, wherein the identifying device has a memory, in which an identification code that is unique worldwide, in particular a universally unique identifier (UUID), is stored in such a way that the identification code can be read out.

10 Claims, 2 Drawing Sheets

TRANSPORT BIN IN AN X-RAY INSPECTION SYSTEM

This nonprovisional application is a continuation of International Application No. PCT/EP2010/005580, which was filed on Sep. 11, 2010, and which claims priority to German Patent Application No. DE 10 2009 048 770.0, which was filed in Germany on Oct. 8, 2009, and which are both herein incorporated by reference.

BACKGROUND OF THE INVENTION

1. Field of the Invention

The invention relates to a transport bin in an X-ray inspection system, an X-ray inspection system that has at least one transport bin, and a method for security inspection.

2. Description of the Background Art

German patent application DE 10 2009 015 606, which is incorporated herein by reference, describes X-ray systems that are used to inspect the hand luggage of airline passengers for illegal or hazardous contents. For this purpose, an X-ray image of the luggage item to be inspected is produced at an initial inspection station with an X-ray device. Luggage items that cannot be unambiguously classified as non-suspicious based on the X-ray image are opened and rechecked by another operator. For this purpose, the operator at the recheck station has a display screen on which the previously produced X-ray image is displayed. Since the initial inspection station with the X-ray device and the recheck station generally are spatially separated, the problem arises of rapidly and reliably identifying and displaying at the recheck station the X-ray image corresponding to the luggage item to be inspected.

The objects to be inspected are placed in transport bins that have an identification device permanently attached to the bin. The identification device contains an unambiguous identifier for the transport bin. The identification device is, for example, an RFID transmitter, in particular an RFID transponder, a bar code, or lead symbols. The identifier of the transport bin during the inspection process also uniquely identifies the luggage item.

The X-ray system includes, among other things, an initial inspection station, a recheck station, and at least one transport bin. Each transport bin has an unambiguous identifier. The initial inspection station has an X-ray device for creating an X-ray image, a device for reading out the identification device of the transport bin, and a device for associating the X-ray image with the transport bin. The X-ray image is associated with the transport bin through the identifier of the transport bin. The transport bin identifier is ascertained in that the identification device is read out.

The X-ray device comprises an X-ray apparatus with at least one X-ray source and at least one X-ray detector in a radiopaque housing, as well as an operating and display apparatus. An X-ray image of the luggage item is computed from the output signal of the X-ray detector and is displayed on the display apparatus.

The device for reading out the identification device of the transport bin can be, for example, an RFID receiver or a bar code reader. These devices are advantageously located in the vicinity of the X-ray apparatus. Alternatively or in addition, the device for reading out the identification device of the transport bin is an image processing routine that extracts the identifier from the X-ray image.

The recheck station has a device for reading out the identification device of the transport bin, and a device for displaying the X-ray image associated with the transport bin. The display device preferably is connected to the X-ray device of the initial inspection station in order to retrieve from there the X-ray image to be displayed.

The device for reading out the identification device at the recheck station is, for example, an RFID receiver or a bar code reader. Alternatively or in addition, the device for reading out the identification device of the transport bin is an optical input device such as a camera. The input device either recognizes the lead symbols directly, or recognizes a legend that contains the same identifier as the lead symbols.

During the security inspection of an object, the object is first placed in a transport bin. Next, an X-ray image of the object is made and evaluated, for example by an operator. In addition, the identifier of the transport bin is read and automatically associated with the corresponding X-ray image. Then the transport bin is transported to a recheck station, the identifier of the transport bin is determined, and the X-ray image associated with the transport bin's identifier is displayed.

In the conventional systems, under certain circumstances errors can occur in associating the bins, which is to say the luggage items, with the corresponding X-ray images at the recheck stations, when multiple X-ray inspection units are used in parallel and the transport bins are exchanged among them. If an image is produced with a transport bin at a first unit, and the bin is subsequently used in a second unit, then it can occur during a recheck in the second unit that either the last image recorded in the first unit with the transport bin is displayed, or that two transport bins with the same identifier are present in the second unit.

SUMMARY OF THE INVENTION

It is therefore an object of the invention to provide a transport bin in an X-ray inspection system with which an erroneous association of the transport bin with an X-ray image taken of it is precluded at the recheck.

This object is attained according to an embodiment of the invention in that the transport bin has identification device with a memory in which a globally unique identification code is stored in a readable manner.

A Universally Unique Identifier (UUID) can be stored in a readable manner as the identification code.

The UUID can be stored as the identification code in the electronic memory of an RFID transponder permanently attached to the bin before or during the first use of the applicable transport bin in an X-ray inspection system. The UUID is a unique identifier that makes it possible to uniquely associate a transport bin with an X-ray image, even if the bin is later used at a different X-ray unit.

Software generators for creating UUIDs are known. Since a UUID is unique in time and space, information items identified with UUIDs can be combined in a single database without conflicts arising.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
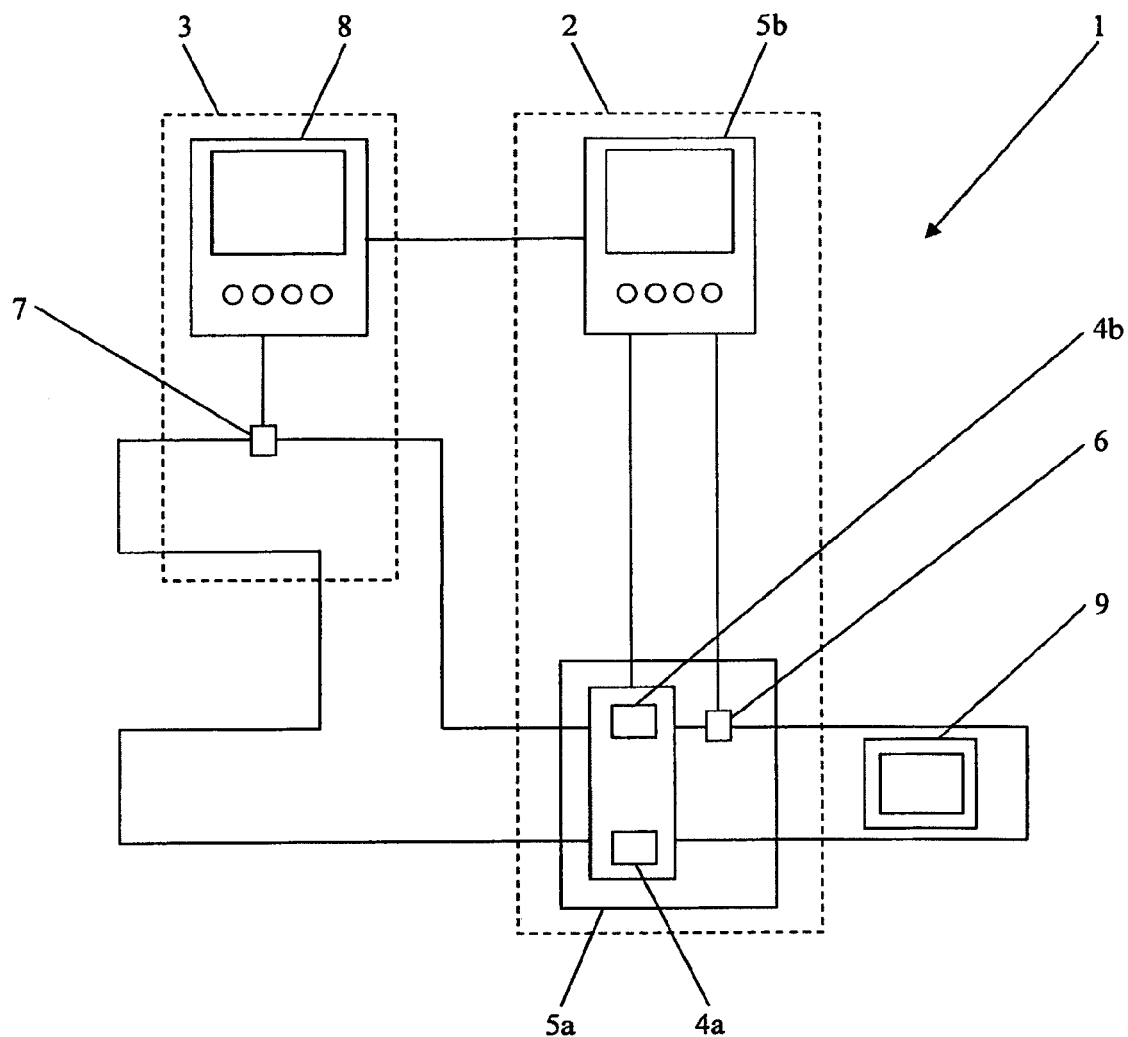
FIG. 1 illustrates an X-ray inspection system.
Figure 2:
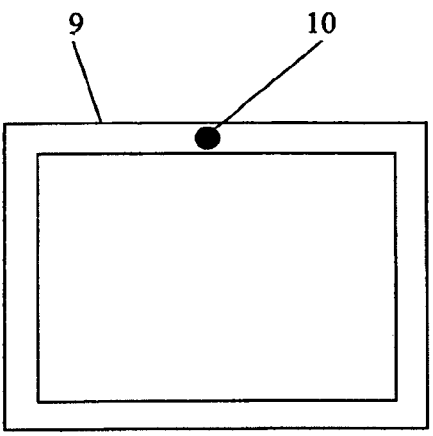
FIG. 2 illustrates a transport bin with RFID transponder.

FIG. 1 schematically shows an X-ray inspection system 1 with an initial inspection station 2 and a recheck station 3. The initial inspection station 2 comprises an X-ray device 5 with an X-ray apparatus 5a and an operating and display apparatus 5b, a device 6 for reading out an identification device of a transport bin 9, and a device for associating an X-ray image with the transport bin 9. The X-ray apparatus 5a contains an X-ray source 4a and an X-ray detector 4b in a radiopaque housing. The recheck station 3 comprises an operating and display apparatus 8 and a device 7 for reading out the identification device of the transport bin 9.

An object to be inspected is placed in the transport bin 9, and transported together therewith through the X-ray apparatus 5a. The object and the transport bin 9 are exposed to X-rays from the X-ray source 4a. The X-ray detector 4b routes the intensity of the transmitted X-rays to the operating and evaluation apparatus 5b, which calculates and displays an X-ray image therefrom. In addition, the identifier of the transport bin 9 is ascertained by the device 6 and the X-ray image is associated with the identifier.

If the object cannot be classified as non-suspicious by the operator of the initial inspection station 2, the transport bin 9 with the object is delivered to the recheck station 3. There, the identifier of the transport bin 9 is ascertained, and the X-ray image associated with the identifier, and thus with the object, is displayed on the operating and display apparatus 8.

The transport bin 9 has an identifier that contain a memory in which a globally unique identification code, preferably a Universally Unique Identifier (UUID), is stored in a readable manner. The applicable UUID was generated in a known manner as a globally unique identification code before or during the first use of the transport bin 9 in an inspection unit.

Preferably, each transport bin 9 has as identification device an RFID transponder with an electronic memory in which a UUID was stored in a readable manner as the identification code before the first use.

The RFID transponder 10 broadcasts the UUID of a transport bin 9 on request. In the event that it has its own power supply, it can also continuously broadcast the identification code. The device 6 and 7 shown in the drawing for reading out the identification device are thus designed as RFID receivers.

Figure 3:
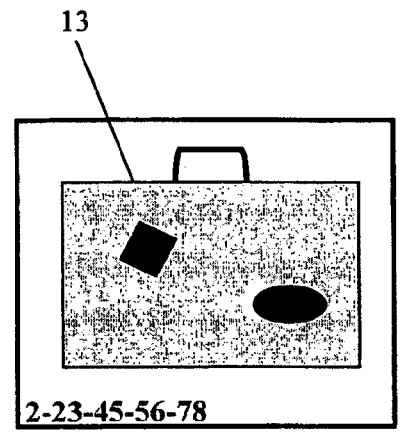
FIG. 3 illustrates an X-ray image when a transport bin is used.

An exemplary X-ray image is shown in FIG. 3. In addition to the contour of the object 13 to be inspected, the UUID is also shown as a sequence of digits in the X-ray image. The UUID of the X-ray image corresponds to the UUID of the transport bin 9, so that a unique association can be made for the X-ray image. When a transport bin 9 arrives at the recheck station 3, the UUID is read out and the associated image is displayed on the display device 8.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A transport bin for an X-ray inspection system, the transport bin comprising:
   an identification device having a bin-specific identifier permanently attached to the bin; and
   a memory arranged in the identification device, a globally unique identification code being stored in the memory in a readable manner,
   wherein the globally unique identification code is assigned to an x-ray image depicting contents of the transport bin wherein the globally unique identification code is depicted in the x-ray image.

2. The transport bin according to claim 1, wherein a Universally Unique Identifier is stored as the globally unique identification code.

3. The transport bin according to claim 1, wherein the identification device is an RFID transponder with an electronic memory in which the globally unique identification code is stored.

4. The transport bin according to claim 3, wherein the globally unique identification code is generated before or during the first use of the transport bin.

5. The transport bin according to claim 1, wherein the x-ray image and the globally unique identification code are stored in a single database.

6. An X-ray inspection system, comprising:
   at least one transport bin, the transport bin comprising:
      an identification device having a bin-specific identifier permanently attached to the bin; and
      a memory arranged in the identification device, a globally unique identification code being stored in the memory in a readable manner;
   an initial inspection station with an X-ray device for creating an X-ray image;
   a reading device configured to read out the identification device of the transport bin;
   a device for associating the X-ray image with the globally unique identification code of the identification device of the transport bin;
   a recheck station with a further reading device configured to read out the identification device of the transport bin; and
   an apparatus configured to display the X-ray image associated with the globally unique identification code of the identification device of the transport bin wherein the globally unique identification code is depicted in the x-ray image.

7. The X-ray inspection system according to claim 6, further comprising a conveyor configured to transport the transport bin between the X-ray device and an X-ray detector.

8. The x-ray inspection system according to claim 6, wherein the x-ray image and the globally unique identification code are stored in a single database.

9. A method for security inspection of an object, in particular hand luggage, the method comprising:
   placing the object in a transport bin, the transport bin comprising:
      an identification device having a bin-specific identifier permanently attached to the bin; and
      a memory arranged in the identification device, a globally unique identification code being stored in the memory in a readable manner;
   taking an X-ray image of the object;

evaluating the X-ray image;
ascertaining the bin-specific identifier of the transport bin;
automatically associating the X-ray image with the globally unique identification code of the identification device of the transport bin;
transporting the transport bin to a recheck station;
ascertaining the bin-specific identifier of the transport bin; and
displaying the X-ray image associated with the globally unique identification code of the identification device of the transport bin wherein the globally unique identification code is depicted in the x-ray image.

10. The method according to claim 9, wherein the x-ray image and the globally unique identification code are stored in a single database.

* * * * *